United States Patent [19]

Dean et al.

[11] Patent Number: 4,582,700

[45] Date of Patent: Apr. 15, 1986

[54] PRODUCTS AND PROCESSES

[75] Inventors: Richard T. Dean, Chesterfield; Fredrick W. Miller, Kirkwood; Dennis W. Wester, Florissant, all of Mo.

[73] Assignee: Mallinckrodt, Inc., St. Louis, Mo.

[21] Appl. No.: 528,487

[22] Filed: Sep. 1, 1983

[51] Int. Cl.$^4$ .................. A61K 43/00; A61K 49/00; C07F 9/02

[52] U.S. Cl. .................. 424/1.1; 260/502.4 P; 424/9

[58] Field of Search ............... 260/502.4 P; 424/1.1, 424/9

[56] References Cited

U.S. PATENT DOCUMENTS

| | | | |
|---|---|---|---|
| 4,233,284 | 11/1980 | Fawzi | 424/1.1 |
| 4,247,534 | 1/1981 | Bevan | 424/1.1 |
| 4,432,963 | 2/1984 | Bevan | 424/1.1 |
| 4,451,450 | 5/1984 | Subramanyam | 424/1.1 |
| 4,455,291 | 6/1984 | Tweedle | 424/1.1 |
| 4,481,184 | 11/1984 | Kronauge et al. | 424/1.1 |

OTHER PUBLICATIONS

Jones et al, J. Nucl. Med, 16(1975) 540.
Deutsch et al, J. Nucl Med, 23(1982) p. 9.
Deutsch et al, J. Nucl Med, 22(1981) 897–907.
Nishiyama et al, J. Nucl Med, 23(1982) 1093–1101.
Nishiyama et al, J. Nucl Med, 23(1982) 1102–10.

*Primary Examiner*—Christine M. Nucker
*Attorney, Agent, or Firm*—R. J. Klostermann; L. N. Goodwin

[57] ABSTRACT

Novel technetium [99m](I) complexes useful as imaging agents.

33 Claims, No Drawings

PRODUCTS AND PROCESSES

The present invention relates to new complexes, processes for their preparation, imaging compositions containing such complexes and methods of imaging utilizing such imaging compositions.

An object of the present invention is to provide complexes which are useful as imaging agents more particularly, myocardial imaging agents. Complexes of the invention are technetium[99m](I) complexes of organo trisubstituted trivalent phosphorus compounds wherein six phosphorus atoms are bound to the technetium and each phosphorus is bonded through at least one oxygen to a carbon, i.e., P—O—C and are illustrated by the following formulae:

   1 wherein $R^1$, $R^2$ and $R^3$ are independently any non-deleterious, chemically suitable, pharmaceutically acceptable substituent including, (1) substituted or unsubstituted alkyl, e.g., containing from about 1 to 15 carbon atoms, including lower alkyl such as methyl, ethyl, propyl, butyl, etc.; (2) substituted or unsubstituted alkoxy, e.g., containing from about 1 to 10 carbon atoms, including lower alkoxy such as methoxy, ethoxy, propoxy, butoxy, and lower alkoxy lower alkyl such as methoxymethyl, ethoxyethyl, ethoxybutyl, etc.; and provided each phosphorous is bonded through at least one oxygen to a carbon. $A^-$ is any non-deleterious, chemically suitable, phamaceutically acceptable anion including halogen, such as $Cl^-$, $Br^-$, $F^-$, $I^-$, $ClO_4^-$, or $BF_4^-$ with $Cl^-$, $H_2PO_4^-$, $HPO_4^{--2}$ and $PO_4^-$ being preferred,

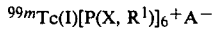   2 wherein X is any bridging non-deleterious, chemically suitable, pharmaceutically acceptable substituent including (1) substituted or unsubstituted alkylenedioxy e.g., containing from about 1 to about 20 carbon atoms including lower alkylenedioxy such as methylenedioxy, 1,2-ethylenedioxy, 1,3-propylenedioxy etc.; and (2) bridging oxyalkyl, containing from about 1 to about 20 carbon atoms including e.g., lower oxyalkyl such as 3-oxypropyl, 4-oxybutyl etc.; $R^1$ has the same meaning as set forth above, provided each phosphorous is bonded through at least one oxygen to a carbon. $A^-$ has the same meaning as set forth above,

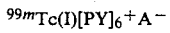   3 wherein Y is any trivalent bridging non-deleterious, chemically suitable, pharmaceutically acceptable substituent including (1) substituted or unsubstituted tri(oxyalkylene)alkane e.g., containing from about 1 to about 20 carbon atoms including lower tri(oxyalkylene)alkane such as tri(oxymethylene)methane; 1,1,1-tri(oxymethylene)ethane, 1,1,1-tri(oxymethylene)propane, etc., (2) substituted or unsubstituted bridging oxydialkyl e.g., containing from about 1 to about 20 carbon atoms including lower oxydialkyl such as 3-oxymethylene1,5-pentyl; 3-methyl-3-oxymethylene-1,5-pentyl, etc., and (3) substituted or unsubstituted briding dioxyalkyl e.g., containing 1 to about 20 carbon atoms including lower dioxyalkyl such as 1,1-di(oxymethylene)-3-propyl, 1,1-di(oxymethylene)-1-methyl-3-propyl etc.; provided each phosphorus is bonded through at least one oxygen to a carbon. $A^-$ has the same meaning as above,

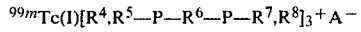   4 wherein $R^4$, $R^5$, $R^7$ and $R^8$ are independently any non-deleterious, chemically suitable, pharmaceutically acceptable substituent including, (1) substituted or unsubstituted alkyl, e.g., containing from about 1 to 15 carbon atoms, including lower alkyl such as methyl, ethyl, propyl, butyl, etc.; (2) substituted or unsubstituted alkoxy, e.g., containing from about 1 to 10 carbon atoms, including lower alkoxy such as methoxy, ethoxy, propoxy, butoxy, and lower alkoxy lower alkyl such as methoxymethyl, ethoxyethyl, ethoxybutyl, etc.; and provided each phosphorous is bonded through at least one oxygen to a carbon. $R^6$ is any non-deleterious chemically suitable pharmaceutically acceptable linking substituent including (1) substituted or unsubstituted alkylene e.g., containing 1 to 10 carbons including lower alkylene such as methylene, propylene, butylene, etc., (2) oxygen; (3) substituted or unsubstituted alkylenedioxy e.g., containing 1 to 10 carbon atoms including lower alkylenedioxy such as methylenedioxy, ethylenedioxy, butylenedioxy, etc. and (4) substituted or unsubstituted oxyalkylene, e.g., containing 1 to 10 carbon atoms including lower oxyalkylene such as oxymethylene, oxyethylene, etc. $A^-$ has the same meaning as set forth above, and

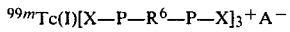   5 wherein each X has the same meaning as set forth above and may be the same or different. $R^6$ and $A^-$ have the same meaning as set forth above; provided each phosphorus is bonded through at least one oxygen to a carbon. The complexes of this invention are useful as imaging agents, e.g., for imaging the heart, liver, lung or kidneys.

The complexes of this invention are prepared according to the process of this invention by reacting one of the aforementioned organo trisubstituted trivalent phosphorus compounds with pertechnetate (preferably anhydrous pertechnetate) under technetium[99m](I) complex forming reaction conditions preferably in an inert non-aqueous solvent. The solvent is removed for example by evaporation. The complexes are then prepared for administration by dissolving or suspending them in a pharmaceutically acceptable vehicle. The organo trisubstituted trivalent phosphorus compounds are old compounds and readily available. For example, they can be prepared by the procedure described in the following references:

1. Boros, E. J., Coskran, K. J., King, R. W., Verkade, J. G., J. Am. Chem Soc. 88 1140 (1966).
2. Blackburn, G. M., Cohen, J. S., Lord Todd, Tetrahedron Letters No. 39, 2873–2879 (1964).
3. Arbuzov, A. E., Zoroastrova, V. M., Rizpolozhenskii, N. I., Izvestiya Akademii Nauk SSSR, Seriya Khimicheskaya, 208-18 (1948).
4. Mathieu, R., Poilblanc, R., Inorganic Chemistry 11, 1858 (1972).
5. Abramov, V. S., Tryapitsyna, N. F., Zhur. Obshchei Khim. 19, 929–38 (1949).

The organo trisubstituted trivalent phosphorous compound is believed to act as the reducing agent for the technetium. Preferred organo substituted trivalent phosphorus compounds include $(CH_3O)_3P$, $(CH_3O)_2PCH_3$, $(CH_3O)P-(CH_3)_2$, and $(CH_3CH_2O)_3P$. Others include:

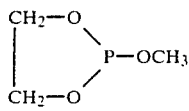

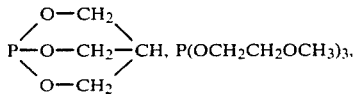

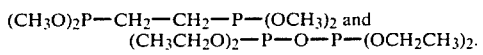

The pertechnetate may be obtained from a generator of the nature illustrated by U.S. Pat. No. 3,369,121, 3,535,085 or 4,296,785. As mentioned, it is preferred to use anhydrous pertechnetate. Anhydrous pertechnetate may be obtained by evaporating the eluate from the aforementioned generator.

Alternatively, the eluate can be applied to a calcium sulfate (anhydrous) column sufficient to bind all the water of the eluate. The column is then eluted with an inert organic solvent such as an oxygen containing material including ketones, e.g., acetone, alcohols, e.g., methanol, ethanol, and esters, e.g., ethyl acetate and ethers, e.g., tetrahydrofuran and dioxane to obtain an anhydrous solution of pertechnetate, preferably sodium pertechnetate. Alternatively, the column may be packed with other drying agents such as sodium sulfate, magnesium sulfate or other molecular sieves.

The source of the anion may be from the pertechnetate from the generator, from the reaction products or from external additions of anion. The amount of the anion is not critical provided it is present in a technetium[99m](I) complex forming amount.

As mentioned, the reaction is carried out under technetium[99m](I) complex forming conditions including technetium complex forming temperatures, e.g., 20° C. to 100° C. at reaction times of from about 25 minutes to several hours. The organo trisubstituted trivalent phosphorus compounds are used in technetium complex forming amounts, usually in large excesses preferably more than a tenfold excess over the pertechnetate. Pertechnetate is used in technetium complex forming amounts and is usually present in an amount from about $10^6$ to about $10^{12}$ molar amounts.

A further feature of the present invention is a imaging composition containing a technetium[99m](I) complex of this invention in an amount sufficient for imaging together with a pharmaceutically acceptable radiological vehicle. Myocardial imaging compositions are preferred.

Pharmaceutically acceptable radiological vehicles include those that are suitable for injection such as human serum albumin, aqueous buffer solutions, e.g., tris(hydroxymethyl) aminomethane (and its salts), phosphate, citrate, bicarbonate, etc., sterile water for injection, physiological saline, and balanced ionic solutions containing chloride and/or bicarbonate salts of normal blood plasma cations such as $Ca^{+2}$, $Na^+$, $K^+$ and $Mg^{+2}$. Other buffer solutions are described in Remington's Practice of Pharmacy, Eleventh Edition for example on page 170.

The concentration of the imaging agent of the present invention in the pharmaceutically acceptable vehicle is a sufficient amount to provide satisfactory imaging. For example, when using aqueous solutions the dosage is about 1.0 to about 20 millicuries.

The imaging composition is administered so that the imaging agent of the present invention remains in the living animal body for about 1 to about 3 hours, although both shorter and longer residence periods are normally acceptable. The composition may thus be formulated for imaging conveniently in vials or ampoules containing 1 to 10 ml of an aqueous solution.

The imaging compositions may be used in the usual way in imaging procedures. For example, a sufficient amount of the imaging composition to provide adequate imaging is injected into the subject and then the subject is scanned with a suitable machine, for example a gamma camera.

The complexes of this invention may be prepared in accordance with the procedures set out below. All temperature designations are in degrees centigrade.

EXAMPLES

Example 1.

Hexakis(trimethylphosphite) technetium[99m](I) Complex

Sodium pertechnetate solution (10 ml) was eluted from an Ultra-Technekow ® UTK-FM ® technetium-99m generator using 0.9% NaCl solution. The water was removed in vacuo at 35–50° on a rotary evaporator. To the dry residue was added 7.5 ml of dry methanol. The mixture was agitated and the methanolic solution of Na $^{99m}TcO_4$ removed by decanting.

The complex was formed by adding methanol (3 ml), trimethylphosphite (1.5 ml) and Na $^{99m}TcO_4$ (3 ml of solution prepared as described above) to a 10 ml vial. The vial was fitted with a rubber stopper and sealed under argon. The vial was heated in a boiling water bath for 20 minutes.

Following the heating step the vial was assayed using ascending paper chromatography with 3MM Whatman paper in 0.9% NaCl solution (a single spot) and MeOH (a single spot). Electrophoresis at pH 7.5 in an aqueous buffer showed a single cationic peak. Detection was performed radiometrically and accounted for total radioactivity spotted. This material was prepared for pharmacological evaluation by removal of the solvent by evaporation and reconstituting with water or saline for injection.

Example 2.

Hexakis(dimethylmethylphosphonite) technetium[99m](I) Complex

This complex was prepared in essentially the same manner as in Example 1, substituting dimethylmethylphosphonite for trimethylphosphite.

Ascending paper chromatography was performed in 0.9% NaCl solution (a single spot) and methanol (a single spot $R_f=0.95$). Little movement of this complex was noted by electrophoresis.

This compound was prepared for pharmacological evaluation as described in Example 1.

Example 3.

Synthesis of $^{99}Tc[P(OCH_3)_3]_6B(C_6H_5)_4$

All manipulations were carried out under argon, using syringe techniques for transfers. Methanol was dried over magnesium and distilled under argon before use. Trimethylphosphite (Aldrich Chemical Company, Inc., Milwaukee, Wis.) was dried with sodium and distilled under argon. Sodium pertechnetate was prepared by adding a slight stoichiometric excess of sodium hydroxide to a solution of ammonium pertechnetate (Oak Ridge National Laboratory, Oak Ridge, Tenn.), evaporating to dryness and recrystallizing the white solid from absolute ethanol. Sodium tetraphenylborate (Aldrich Chemical Company, Inc., Milwaukee, Wis.) was recrystallized from a xylene-acetone mixture.

To a 200 ml glass pressure bottle were added $P(OCH_3)_3$ (10 ml, 10.52 g, 84.8 mmole) and MeOH (30 ml). The solution was purged with argon. In a 30 ml serum vial were placed $NaTcO_4$ (181 mg, 1 mmole) and MeOH (3 ml). The vial was capped and the solution was taken to dryness under a stream of argon. The resulting solid, $NaTcO_4$, was dissolved in MeOH (10 ml). The $NaTcO_4$ solution was then added to the $P(OCH_3)_3$ solution and the dark red mixture was sealed in the reactor. The reactor was placed in a water bath at 90° C. for 30 minutes, during which the color of the solution changed from dark red to orange to yellow. The reactor was removed from the water bath and cooled to room temperature. The solution was placed on a rotary evaporator and taken to dryness. The resulting purple solid was dissolved in MeOH (4 ml) and added to a solution of $NaB(C_6H_5)_4$ (1.15 g, 3.4 mmole) in MeOH (2 ml), producing a white precipitate. The precipitate was collected by filtration, washed with petroleum ether and recrystallized from MeOH to give crystalline $Tc[P(OCH_3)_3]_6B(C_6H_5)_4$.

Satisfactory analyses were obtained on recrystallized samples. Found (calculated): P, 15.72 (15.99); C, 43.40 (43.39); H, 6.47 (6.42).

Nuclear magnetic resonance spectral data are consistent with the proposed structure.

Mass spectral results are consistent with the proposed structure.

Infrared spectral data are consistent with the proposed structure.

Example 4.

Reaction of Triethylphosphite and Sodium Pertechnetate-99m

Sodium pertechnetate solution (10 ml) was eluted from an Ultra-Technekow ® UTK-FM ® technetium-99m generator using 0.9% NaCl solution. The water was removed in vacuo at 30–50° on a rotary evaporator. To the dry residue was added 7.5 ml of ethanol. The mixture was agitated and the ethanolic solution of $Na^{99m}TcO_4$ removed by decanting.

The complex was formed by adding ethanol (3 ml), triethylphosphite (0.35 ml) and $Na^{99m}TcO^4$ (0.75 ml of solution prepared as described above) to a 10 ml vial. The vial was fitted with a rubber stopper and sealed under argon. The vial was heated in a boiling water bath for 20 minutes.

Following the heating step the vial was assayed using ascending paper chromatography with 3MM Whatman paper in 0.9% NaCl solution (a single spot) and MeOH (a single spot at $R_f=0.9$). Electrophoresis at pH 7.5 in an aqueous buffer showed little movement for this complex. Detection was performed radiometrically and accounted for total radioactivity spotted.

Example 5.

Reaction of Triisopropylphosphite and Sodium Pertechnetate-99m

This complex was prepared in essentially the same manner as the triethylphosphite complex, substituting dried isopropanol for ethanol and triisopropylphosphite for triethylphosphite.

Ascending paper chromatography was performed in 0.9% NaCl solution (a single spot) and methanol (a single spot at $R_f=0.94$). Electrophoresis showed little movement for this complex.

Example 6.

Reaction of Tri-n-butylphosphite and Sodium Pertechnetate-99m

This complex was prepared in essentially the same manner as the triethylphosphite complex substituting n-butanol for ethanol and tri-n-butylphosphite for triethylphosphite.

Ascending paper chromatography was performed in 0.9% NaCl (a single spot) and methanol (a single spot at $R_f=0.93$).

Example 7.

Reaction of 4-Hydroxymethyl-2,6,7-trioxa-1-phosphabicyclo [2.2.2]octane and Sodium Pertechnetate-99m This complex was prepared in essentially the same manner as the triethylphosphite complex substituting methanol for ethanol and 4-hydroxymethyl-2,6,7-trioxa-1-phosphabicyclo [2.2.2]octane for triethylphosphite.

Ascending paper chromatography was performed in 0.9% NaCl (a single spot) and methanol (a single spot at $R_f$-0.93).

Example 8.

Pharmacological Evaluation of the Technetium[99m](I) Complexes

The following pharmacological studies were conducted on Complex (A), prepared by the method of Example 1; Complex (B), prepared by the method of Example 2; Complex (C) prepared by the method of Example 4; Complex (D) prepared by the method of Example 6; and Complex (E) prepared by the method of Example 7. Where indicated, Thallium-201 was used for comparative purposes.

Biodistribution of A, B, C, D, and E in Rats

The biodistribution of the experimental $^{99m}Tc(I)$ complexes in rats was compared with Thallium-201, currently the radionuclide of choice for myocardial perfusion imaging. Complex A was supplied as a vacuum-evaporated preparation and reconstituted with 0.9% Sodium Chloride, Injection, U.S.P. The $^{99m}Tc(I)$ complexes and $^{201}TlCl$ solutions were diluted to concentrations of 12.5 uCi/ml with 0.9% Sodium Chloride, Injection, U.S.P. for dosing. Groups of 4–12 female Sprague-Dawley rats with body weights ranging from 180–231 g received single intraveneous injections of 25uCi/kg of Complex A, Complex B, Complex C, Complex D, Complex E, or $^{201}TlCl$.

Animals were sacrificed 5 minutes after dosing and radioactivity concentrations were determined by gamma scintillation spectroscopy in blood, heart, liver, lungs, kidney and skeletal muscle. As a measurement of selectivity of myocardial uptake, heart/blood, heart/liver and heart/lung tissue ratios were determined. Five minute rat biodistribution data are summarized in Tables 1 and 2.

Complex B exhibited the greatest absolute heart uptake of the $^{99m}$Tc(I) complexes tested. Complex A appeared to be rapidly cleared from the blood, attaining substantially lower blood levels than observed for Complex B, Complex C, Complex D, Complex E and $^{201}$TlCl. Complex A exhibited the highest degree of selectivity for myocardial uptake of the $^{99m}$Tc-chelates and the 5 minute heart/blood and heart/lung ratios were superior to those obtained with $^{201}$TlCl (Table 2).

A second rat biodistribution study was conducted to determine the time course of myocardial retention and excretion characteristics of Complex A. Complex A was reconstituted with 0.9% Sodium Chloride, Injection, U.S.P. to yield solution concentrations of 12.5 or 100 uCi/ml. Female Sprague-Dawley rats, 4 per time point, with body weights ranging from 181–224 g, received single intraveneous injections of either 25 or 200 uCi/kg of Complex A. Animals were sacrificed at 5, 15, 45 and 90 minutes and at 4 and 24 hours after dosing. Tissue samples, as previously described, were assayed for radioactivity. In addition, urine samples collected from rats sacrificed at 4 and 24 hours and fecal samples obtained at 24 hours were assayed for radioactivity. Biodistribution results are summarized in Table 3.

A one-compartment open pharmacokinetic model was used for estimating heart, liver and lung clearance half-lives for Complex A in the rat. The estimated half-lives were 14.4 hr., 24 min. and 40 min. for heart, liver and lung, respectively. The rapid blood, liver and lung clearance of Complex A resulted in outstanding heart/non-target tissue ratios at later time points as summarized in Table 4.

A total of 25% of the administered dose of radioactivity was recovered in excreta within a 24-hour period with approximately equal amounts in urine and feces.

Myocardial Imaging with COMPLEX A

A computerized gamma camera system was used for acquiring anterior myocardial images with Complex A. Imaging experiments were conducted in a female, pentobarbital-anesthetized dog (8.0 kg) and a Ketamine/Xylazine-anesthetized female New Zealand white rabbit (3.0 kg). The dog and rabbit received intraveneous injections of 1.0 and 2.0 mCi. respectively of a diluted Complex A methanol preparation and sequential images were acquired for 60 minutes after dosing.

Imaging with Complex A in the dog revealed excellent myocardial uptake resulting in a "donut-like" myocardial appearance. Myocardial images persisted throughout the 60-minute imaging period. Substantial renal and hepatic uptake of Complex A was also noted in the dog. Hepatic clearance of Complex A resulted in substantial gallbladder accumulation of radioactivity within 30 minutes after injection.

In the rabbit, excellent persistent myocardial visualization was observed. Substantial hepatic and renal uptake was noted. Hepatic uptake of radioactivity was maximal at 5 minutes and the apparent hepatic elimination half-life was 15 minutes with intestinal accumulation of activity evident within 2–4 minutes after intraveneous administration.

TABLE 1

COMPARATIVE 5 MINUTE RAT BIODISTRIBUTION of COMPLEXES A-E AND $^{201}$TlCl

| Test Substance | Number of Animals | Mean % Dose/g or ml | | | | | |
|---|---|---|---|---|---|---|---|
| | | Heart | Blood | Liver | Lung | Kidney | Muscle |
| A | 12 | 3.33 | 0.07 | 0.92 | 1.93 | 6.26 | 0.32 |
| B | 4 | 4.06 | 0.42 | 1.86 | 8.38 | 5.96 | 0.05 |
| C | 4 | 0.77 | 0.75 | 4.86 | 4.43 | 1.37 | 0.32 |
| D | 4 | 0.17 | 0.40 | 4.53 | 20.83 | 0.41 | 0.05 |
| E | 4 | 0.33 | 0.97 | 0.29 | 0.64 | 3.11 | 0.21 |
| $^{201}$TlCl | 4 | 6.35 | 0.26 | 1.01 | 4.69 | 6.53 | 0.82 |

TABLE 2

RAT HEART/NON-TARGET TISSUE RATIOS 5 MINUTES AFTER DOSING WITH COMPLEXES A-E and $^{201}$TlCl

| Test Substance | Number of Animals | Mean Tissue Ratios | | |
|---|---|---|---|---|
| | | Heart/Blood | Heart/Liver | Heart/Lung |
| A | 12 | 52.20 | 3.69 | 1.72 |
| B | 4 | 14.34 | 2.25 | 0.49 |
| C | 4 | 1.25 | 0.18 | 0.19 |
| D | 4 | 0.51 | 0.04 | 0.01 |
| E | 4 | 0.40 | 1.16 | 0.53 |
| $^{201}$TlCl | 4 | 24.31 | 6.31 | 1.35 |

TABLE 3

BIODISTRIBUTION of COMPLEX A at VARIOUS TIMES FOLLOWING INTRAVENEOUS ADMINISTRATION

| Time After Dosing | Mean % Dose/g or ml | | | | | |
|---|---|---|---|---|---|---|
| | Heart | Blood | Liver | Lung | Kidney | Muscle |
| 5 min. | 3.05 | 0.10 | 0.83 | 1.57 | 3.81 | 0.51 |
| 15 min. | 3.23 | 0.06 | 0.53 | 1.01 | 6.41 | 0.52 |
| 45 min. | 2.83 | 0.03 | 0.18 | 0.56 | 4.55 | 0.49 |
| 90 min. | 2.89 | 0.02 | 0.07 | 0.33 | 2.70 | 0.59 |
| 4 hr. | 1.99 | 0.01 | 0.03 | 0.13 | 1.19 | 0.49 |
| 24 hr. | 0.97 | 0.01 | 0.02 | 0.06 | 0.74 | 0.42 |

TABLE 4

RAT HEART/NON-TARGET TISSUE RATIOS at VARIOUS TIMES AFTER DOSING with COMPLEX A

| Time After Dosing | Mean Tissue Ratios | | |
|---|---|---|---|
| | Heart/Blood | Heart/Liver | Heart/Lung |
| 5 min. | 29.67 | 3.86 | 1.99 |
| 15 min. | 58.39 | 6.25 | 3.27 |
| 45 min. | 121.8 | 16.77 | 6.02 |
| 90 min. | 190.6 | 41.90 | 9.05 |
| 4 hr. | 206.2 | 58.70 | 15.24 |
| 24 hr. | 117.3 | 49.43 | 16.04 |

What is claimed:

1. A technetium [99m](I) complex selected from the group of complexes having the following formulae:
$$^{99m}Tc(I)[P(R^1,R^2,R^3)]_6{}^+A^- \qquad 1$$

wherein $R^1$, $R^2$ and $R^3$ are independently selected from the group consisting of lower alkyl, lower alkoxy, and lower alkoxy lower alkyl provided each phosphorous is bonded through at least one oxygen to a carbon; and $A^-$ is a non-deleterious, chemically suitable, pharmaceutically acceptable anion;

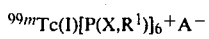  2 wherein X is a bridging substituent selected from the group consisting of lower alkylenedioxy, and lower oxyalkyl; $R^1$ has the same meaning as set forth above, provided each phosphorous is bonded through at least one oxygen to a carbon, and $A^-$ has the same meaning as set forth above;

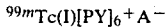  3 wherein Y is a trivalent bridging substituent selected from the group consisting of lower tri(oxyalkylene)alkane, lower oxydialkyl, and lower dioxyalkyl, provided each phosphorous is bonded through at least one oxygen to a carbon; and $A^-$ has the same meaning as set forth above;

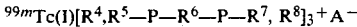  4 wherein $R^4$, $R^5$, $R^7$ and $R^8$ are independently selected from the group consisting of, lower alkyl, lower alkoxy, and lower alkoxy lower alkyl; $R^6$ is a linking substituent selected from the group consisting of lower alkylene, oxygen, lower alkylenedioxy and lower oxyalkylene, provided each phosphorous is bonded through at least one oxygen to a carbon; and $A^-$ has the same meaning as set forth above; and

  5 wherein X, $R^6$ and $A^-$ have the same meaning as set forth above and provided each phosphorous is bonded through at least one oxygen to a carbon.

2. A complex according to claim 1 selected from the group of complexes represented by formula 1 of claim 1.

3. A complex according to claim 2, wherein the anion is selected from the group consisting of $Cl^-$, $H_2PO_4^-$, $HPO_4^{-2}$ and $PO_4^{-3}$.

4. A complex according to claim 3 wherein $R^1$ and $R^2$ are methoxy and $R^3$ is methyl.

5. A complex according to claim 3 wherein $R^1$ and $R^2$ are methyl and $R^3$ is methoxy.

6. A complex according to claim 3 wherein $R^1$, $R_2$ and $R_3$ are ethoxy.

7. A complex according to claim 3 wherein $R^1$, $R^2$ and $R^3$ are methoxy.

8. A complex according to claim 1 selected from the group of complexes represented by formula 2 of claim 1.

9. A complex according to claim 1 selected from the group of complexes represented by formula 3 of claim 1.

10. A complex according to claim 1 selected from the group of complexes represented by formula 4 of claim 1.

11. A complex according to claim 1 selected from the group of complexes represented by formula 5 of claim 1.

12. An imaging composition containing a technetium [99m](I) complex selected from the group of complexes having the following formulae:

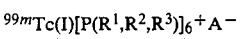  1 wherein $R^1$, $R^2$ and $R^3$ are independently selected from the group consisting of lower alkyl, lower alkoxy, and lower alkoxy lower alkyl provided each phosphorous is bonded through at least one oxygen to a carbon; and $A^-$ is a non-deleterious, chemically suitable, pharmaceutically acceptable anion;

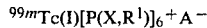  2 wherein X is a bridging substituent selected from the group consisting of lower alkylenedioxy, and lower oxyalkyl; $R^1$ has the same meaning as set forth above, provided each phosphorous is bonded through at least one oxygen to a carbon, and $A^-$ has the same meaning as set forth above;

  3 wherein Y is a trivalent bridging substituent selected from the group consisting of lower tri(oxyalkylene)alkane, lower oxydialkyl, and lower dioxyalkyl, provided each phosphorous is bonded through at least one oxygen to a carbon; and $A^-$ has the same meaning as set forth above;

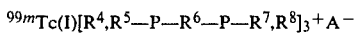  4 wherein $R^4$, $R^5$, $R^7$ and $R^8$ are independently selected from the group consisting of, lower alkyl, lower alkoxy, and lower alkoxy lower alkyl; $R^6$ is a linking substituent selected from the group consisting of lower aklylene, oxygen, lower alkylenedioxy and lower oxyalkylene, provided each phosphorous is bonded through at least one oxygen to a carbon; and $A^-$ has the same meaning as set forth above; and

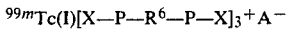  5 wherein X, $R^6$ and $A^-$ have the same meaning as set forth above and provided each phosphorous is bonded through at least one oxygen to a carbon in a sufficient amount to provide satisfactory imaging together with a pharmaceutically acceptable vehicle.

13. A composition according to claim 12 wherein said complex is selected from the group of complexes represented by formula 1 of claim 12.

14. A composition according to claim 13, wherein the anion is selected from the group consisting of $Cl^-$, $H_2PO_4^-$, $HPO_4^{-2}$ and $PO_4{^3}$.

15. A composition according to claim 14 wherein $R^1$ and $R^2$ are methoxy and $R^3$ is methyl.

16. A composition according to claim 14 wherein $R^1$ and $R^2$ are methyl and $R^3$ is methoxy.

17. A composition according to claim 14 wherein $R^1$, $R^2$ and $R^3$ are ethoxy.

18. A composition according to claim 14 wherein $R^1$, $R^2$ and $R^3$ are methoxy.

19. A composition according to claim 12 selected from the group of complexes having formula 2 of claim 12.

20. A composition according to claim 12 selected from the group of complexes represented by formula 3 of claim 12.

21. A composition according to claim 12 selected from the group of complexes represented by formula 4 of claim 12.

22. A composition according to claim 12 selected from the group of complexes represented by formula 5 of claim 12.

23. In a method for imaging wherein a composition containing a technetium [99m](I) complex in a pharmaceutically acceptable vehicle is injected into a living animal body in a sufficient amount to provide adequate imaging and thereafter imaging carried out, the improvement comprising utilizing as the composition a composition containing a technetium [99m](I) complex selected from the group of complexes having the following formulae:

$$^{99m}Tc(I)[P(R^1,R^2,R^3)]_6{}^+A^- \qquad 1$$

wherein $R^1$, $R^2$ and $R^3$ are independently selected from the group consisting of lower alkyl, lower alkoxy, and lower alkoxy lower alkyl provided each phosphorous is bonded through at least one oxygen to a carbon; and $A^-$ is a non-deleterious, chemically suitable, pharmaceutically acceptable anion;

$$^{99m}Tc(I)[P(X,R^1)]_6{}^+A^- \qquad 2$$

wherein X is a bridging substituent selected from the group consisting of lower alkylenedioxy, and lower oxyalkyl; $R^1$ has the same meaning as set forth above, provided each phosphorous is bonded through at least one oxygen to a carbon, and $A^-$ has the same meaning a set forth above;

$$^{b\ 99m}Tc(I)[PY]_6{}^+A^- \qquad 3$$

wherein Y is a trivalent bridging substituent selected from the group consisting of lower tri(oxyalkylene)alkane, lower oxydialkyl, and lower dioxyalkyl, provided each phosphorous is bonded through at least one oxygen to a carbon; and $A^-$ has the same meaning as set forth above;

$$^{99m}Tc(I)[R^4,R^5-P-R^6-P-R^7,R^8]_3{}^+A^- \qquad 4$$

wherein $R^4, R^5, R^7$ and $R^8$ are independently selected from the group consisting of, lower alkyl, lower alkoxy, and lower alkoxy lower alkyl; $R^6$ is a linking substituent selected from the group consisting of lower alkylene, oxygen, lower alkylenedioxy and lower oxyalkylene, provided each phosphorous is bonded through at least one oxygen to a carbon; and $A^-$ has the same meaning as set forth above; and $$^{99m}Tc(I)[X-P-R^6-P-X]_3{}^+A^- \qquad 5$$

wherein X, $R^6$ and $A^-$ have the same meaning as set forth above and provided each phosphorous is bonded through at least one oxygen to a carbon in a sufficient amount to provide satisfactory myocardial imaging together with a pharmaceutically acceptable vehicle.

24. A method according to claim 23 wherein said complex is selected from the group of complexes represented by formula 1 of claim 23.

25. A method according to claim 24 wherein the anion is selected from the group consisting of $Cl^-$, $H_2PO_4{}^-$, $HPO_4{}^{-2}$ and $PO_4{}^{-3}$.

26. A method according to claim 25 wherein $R^1$ and $R^2$ are methoxy and $R^3$ is methyl.

27. A method according to claim 25 wherein $R^1$ and $R^2$ are methyl and $R^3$ is methoxy.

28. A method according to claim 25 wherein $R^1$, $R^2$ and $R^3$ are ethoxy.

29. A method according to claim 25 wherein $R^1$, $R^2$ and $R^3$ are methoxy.

30. A method according to claim 23 selected from the group of complexes represented by formula 2 of claim 23.

31. A method according to claim 23 selected from the group of complexes represented by formula 3 of claim 23.

32. A method according to claim 23 selected from the group of complexes represented by formula 4 of claim 23.

33. A method according to claim 23 selected from the group of complexes represented by formula 5 of claim 23.

* * * * *